(12) United States Patent
Ghosh et al.

(10) Patent No.: US 11,786,633 B2
(45) Date of Patent: Oct. 17, 2023

(54) 3D BIOPRINTED SCAR TISSUE MODEL

(71) Applicant: INDIAN INSTITUTE OF TECHNOLOGY, DELHI, New Delhi (IN)

(72) Inventors: Sourabh Ghosh, New Delhi (IN); Shikha Chawla, New Delhi (IN)

( * ) Notice: Subject to any disclaimer, the term of this patent is extended or adjusted under 35 U.S.C. 154(b) by 426 days.

(21) Appl. No.: 16/768,819

(22) PCT Filed: Nov. 30, 2018

(86) PCT No.: PCT/IN2018/050804
§ 371 (c)(1),
(2) Date: Jun. 1, 2020

(87) PCT Pub. No.: WO2019/106695
PCT Pub. Date: Jun. 6, 2019

(65) Prior Publication Data
US 2021/0170071 A1    Jun. 10, 2021

(30) Foreign Application Priority Data
Nov. 30, 2017    (IN) ............................. 201711043083

(51) Int. Cl.
| | |
|---|---|
| A61L 27/22 | (2006.01) |
| A61L 27/24 | (2006.01) |
| A61L 27/38 | (2006.01) |
| B33Y 10/00 | (2015.01) |
| B33Y 70/10 | (2020.01) |
| B33Y 80/00 | (2015.01) |

(52) U.S. Cl.
CPC ........... *A61L 27/227* (2013.01); *A61L 27/222* (2013.01); *A61L 27/24* (2013.01); *A61L 27/3804* (2013.01); *A61L 27/3895* (2013.01); *A61L 2300/414* (2013.01); *A61L 2300/426* (2013.01); *B33Y 10/00* (2014.12); *B33Y 70/10* (2020.01); *B33Y 80/00* (2014.12)

(58) Field of Classification Search
None
See application file for complete search history.

(56) References Cited

U.S. PATENT DOCUMENTS

| | | |
|---|---|---|
| 2005/0261780 A1 | 11/2005 | Heino |
| 2010/0160917 A1 | 6/2010 | Fitz |
| 2011/0218634 A1 | 9/2011 | Ringeisen |
| 2012/0271418 A1 | 10/2012 | Hollister |
| 2015/0073551 A1 | 3/2015 | Uehlin |
| 2016/0122723 A1* | 5/2016 | Retting ................... A61L 27/60 435/395 |
| 2020/0197179 A1 | 6/2020 | Ghosh |

FOREIGN PATENT DOCUMENTS

| | | |
|---|---|---|
| WO | WO 2018/198138 A1 | 11/2018 |
| WO | WO 2019/106695 A1 | 6/2019 |

OTHER PUBLICATIONS

Das, S., et al., Bioprintable, cell-laden silk fibroin-gelatin hydrogel supporting multilineage differentiation of stem cells for fabrication of three-dimensional tissue constructs, Acta Biomaterialia 11 (2015) 233-246 (Year: 2015).*
Chimene, D., et al., Advanced Bioinks for 3D Printing: A Materials Science Perspective, Annals of Biomedical Engineering, vol. 44, No. 6, Jun. 2016 2090-2102 (Year: 2016).*
Soundararajan, M. & Kannan, S., Fibroblasts and mesenchymal stem cells: Two sides of the same coin?, J Cell Physiol. 2018;233: 9099-9109 (Year: 2018).*
Wilson et al., Control of Scar Tissue Formation in the Cornea: Strategies in Clinical and Corneal Tissue Engineering, J. Funct., Biomater., 3, 642-87 (2012); see May 25, 2023 IDS.*
International Preliminary Report on Patentability, dated Oct. 29, 2019 in International Application No. PCT/IN2018/050264.
International Preliminary Report on Patentability, dated Jun. 2, 2020 in International Application No. PCT/IN2018/050804.
International Search Report and Written Opinion, dated Jul. 17, 2018, International Application No. PCT/IN2018/050264.
International Search Report & Written Opinion, dated Feb. 12, 2019, in International Application No. PCT/IN2018/050804.
Koppenol, D.C., et al., A mathematical model for the simulation of the formation and the subsequent regression of hypertrophic scar tissue after dermal wounding, *Biomech Model Mechanobiol*, vol. 16, pp. 15-32, 2017.
Bloemsma et al., Mortality and causes of death in a burn centre, Burns 34, pp. 1103-1107, 2008.
Chawla et al., Elucidating role of silk-gelatin bioink to recapitulate articular cartilage differentiation in 3D bioprinted constructs, Bioprinting 7, pp. 1-13, 2017.
Chipev et al., "Phenotypic differences between dermal fibroblasts from different body sites determine their responses to tension and TGFβ1," BMC Dermatology, 2, 13, pp. 1-13, 2002.
Corr et al., Biomechanics of Scar Tissue and Uninjured Skin, Advances in Wound Care, vol. 2 No. 2, pp. 37-43, 2013.
Jarmuz et al., Transforming Growth Factor β-1, Myofibroblasts, and Tissue Remodeling in the Pathogenesis of Tracheal Injury: Potential Role of Gastroesophageal Reflux, Ann. Otol. Rhinol. Laryngol., 113, 488-497, 2004.
Karamichos et al., "Human Corneal Fibrosis: An In Vitro Model," Investigative Opthalmology & Visual Science, vol. 51, No. 3, pp. 1382-1388, 2010.
Lewis, J.A., Novel Inks for Direct-Write Assembly of 3-D Periodic Structures, Material Matters, vol. 3 No. 1, pp. 1-28, 2008.
Wilson et al., Control of Scar Tissue Formation in the Cornea: Strategies in Clinical and Corneal Tissue Engineering, J. Funct. Biomater., 3, 642-687, 2012.

\* cited by examiner

*Primary Examiner* — H. Sarah Park
(74) *Attorney, Agent, or Firm* — Knobbe, Martens, Olson & Bear LLP

(57) ABSTRACT

A bioink composition and a 3D bioprinted scar tissue model with the bioink composition closely replicates the physiological and architectural characteristics of naturally occurring scar tissue. The 3D bioprinted scar tissue can be used to test scar resolution treatments among others. Also provided is a method of fabricating the 3D bioprinted scar tissue along with an apparatus for bioprinting the 3D bioprinted scar tissue.

5 Claims, 4 Drawing Sheets

3D BIOPRINTED SCAR TISSUE MODEL

PRIORITY AND CROSS REFERENCE TO RELATED APPLICATIONS

This application is the U.S. National Stage Application under 35 U.S.C. § 371 of International Application No. PCT/IN2018/050804, filed Nov. 30, 2018, designating the U.S. and published in English as WO 2019/106695 A1 on Jun. 6, 2019, which claims the benefit of Indian Patent Application No. IN 201711043083, filed Nov. 30, 2017. Any and all applications for which a foreign or a domestic priority is claimed is/are identified in the Application Data Sheet filed herewith and is/are hereby incorporated by reference in their entirety under 37 C.F.R. § 1.57.

FIELD OF INVENTION

The present disclosure relates to the field of 3D bioprinting in general and fibrotic tissue specific to any organ in particular. This fibrotic in vitro scar tissue construct as described herein can be produced by 3D bioprinting.

BACKGROUND OF INVENTION

Scar forms during the prolonged wound healing response due to chronic inflammation. Depending on the site of injury, scar tissue could be formed externally, such as on the skin and eye, and could also occur in internal organs forming cardiac scars, liver scars, renal scars and tracheal scars among others. Scar tissue has a very distinct appearance owing to its specific structure and composition. As a consequence, scarring of tissue can often have negative effects on the appearance of an injured individual and can have adverse effects on the functionality of organs.

Impaired and prolonged wound healing induces continuous differentiation of fibroblasts to myofibroblasts which demonstrate incessant proliferation and migration, subsequently leading to excessive extracellular matrix (ECM) synthesis, along-with increased and extended contraction of the wound site resulting in a scar (Karamichos et al., Investig. Ophthalmol. Vis. Sci., 51 (2010) 1382-1388). Owing to its inelasticity, this overextended growth impairs the regeneration of normal tissue, which can cause blockages, prevent the movement and contraction of organs, and cause permanent organ disfigurement. For instance, skin scarring leads to loss of physiological function and aesthetics of the patients and even death in extreme cases (Bloemsma et al., Burns, 8(2008) 1103-7). Further, corneal scarring is the prime cause of permanent blindness worldwide (Wilson et al., J. Funct. Biomater., 3(2012) 642-87). In the tracheal lumen, occurrence and progression of subglottic stenosis is triggered by tracheal injury followed by release of proinflammatory cytokines is another example where scar tissue develops in the trachea. In addition, differentiation of tracheal fibroblasts to myofibroblasts causes total destruction or choking of the tracheal lumen due to excessive deposition of connective tissue (Jarmuz et al., Ann. Otol. Rhinol. Laryngol., 113 (2004), 488-97). Renal scarring and scarring of heart tissue is one of the major reasons for kidney and heart failure, respectively. In the diseased heart, cardiomyocytes are lost due to necrotic cell death, further excessive scarring can also cause pulmonary fibrosis. In the kidney, scarring is responsible for end stage glomerulonephritis, while in the liver it can cause cirrhosis.

Researchers and pharmaceutical industries throughout the world are trying to develop scar resolution strategies such as drugs, therapeutics, bioactive molecules and cosmetics, however the problem of scarring still persists. Thus, a major reason for slow progress in scar resolution is attributed to the limited understanding of scar pathophysiology and most importantly the lack of a suitable in vitro model for rapid drug testing.

SUMMARY OF INVENTION

In an aspect of the present disclosure, there is provided a method of fabricating a 3D bioprinted scar tissue, the method comprising: 3D bioprinting at least one layer of a bioink composition, using a computer-assisted design model, wherein the bioink comprises at least one polypeptide, at least one cytokine, and at least one cell population selected form the group consisting of epidermal cells, dermal cells, and tissue specific fibroblastic cells.

In an aspect of the present disclosure, there is provided an apparatus for bioprinting a 3D bioprinted scar tissue comprising: (a) a printing substrate; (b) a 3D bioprinter with at least one nozzle for 3D bioink printing; and, (c) a bioink composition comprising at least one polypeptide, at least cytokine, and at least one cell population selected from the group consisting of epidermal cells, dermal cells, and tissue specific fibroblastic cells.

In an aspect of the present disclosure, there is provided a bioink composition comprising at least one polypeptide, at least one cytokine, and at least one cell population selected from the group consisting of epidermal cells, dermal cells, and tissue specific fibroblastic cells.

In an aspect of the present disclosure, there is provided a 3D bioprinted scar tissue comprising at least one layer of a bioink composition comprising at least one polypeptide, at least one cytokine, and at least one cell population selected from the group consisting of epidermal cells, dermal cells, and tissue specific fibroblastic cells.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE DRAWINGS

The following drawings form a part of the present specification and are included to further illustrate aspects of the present disclosure. The disclosure may be better understood by reference to the drawings in combination with the detailed description of the specific embodiments presented herein.

DETAILED DESCRIPTION OF THE INVENTION

Figure 1:
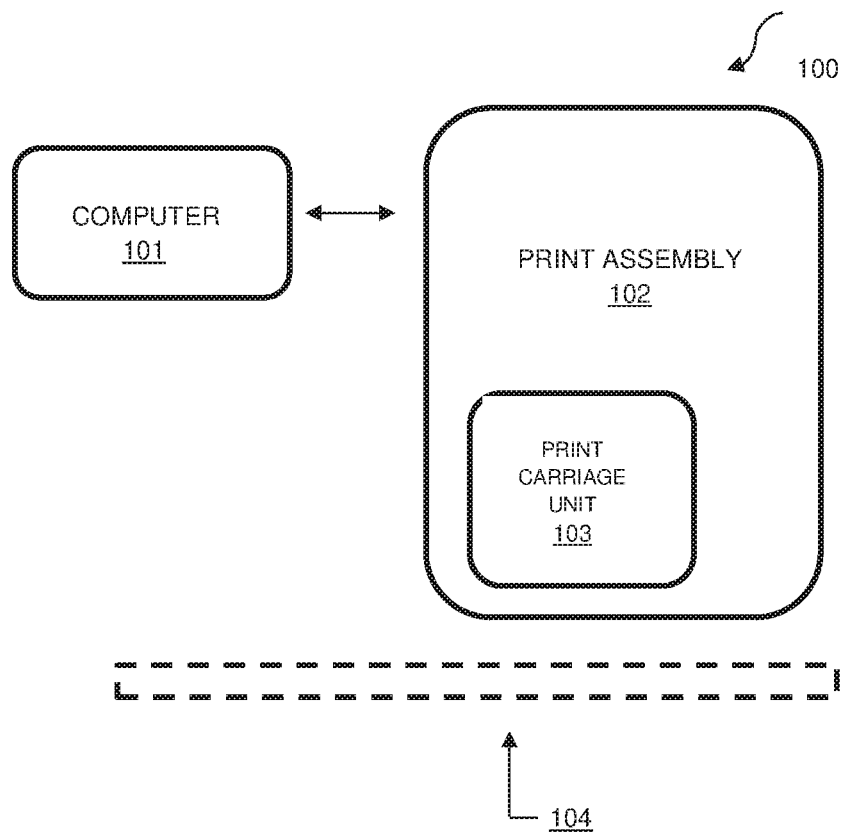
FIG. 1 illustrates a block diagram of an additive manufacturing system (referred to as system 100), in accordance with an embodiment of the present disclosure.

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Healthy skin comprises collagen, a connective tissue, which forms an extended fibrous network which is embedded in an extra-cellular matrix (ECM). Collagen type I, along with elastin, are responsible for the viscoelastic nature of skin and this elasticity is essential to maintain healthy organ functioning and growth.

Full thickness wounding of skin, whether internally or externally, results in the formation of scar tissue. Scar tissue is distinct from normal tissue, primarily with respect to the distribution and alignment of collagen fibres. In scar tissue, collagen fibers are primarily extended in a specific parallel direction, rather than the random organisation which is common in healthy tissue. This fully extended collagen exhibits reduced elasticity and therefore hampers normal organ functioning. Scar tissue also exhibits over expression of collagen which results in its bundled growth overextending normal tissue, often preventing regeneration and normal growth of healthy tissue.

An aim of researchers has long been to understand the biomechanics of scar tissue to mitigate the detrimental effects of scarring. Animal models are routinely used to study scar tissue properties. Murine, rabbit and pig models are the most frequently used animal models. However, these models do not provide sufficient detail in understanding the different aspects of scar tissue development, for example, the temporal sequence of tissue development and wound healing (Con and Hart, Adv. Wound Care, 2(2), 2013, 37-43). Data from such models are not suitable for application to humans as scar tissue exhibits intraspecies and interspecies differences during the wound healing process.

An alternative to the limitations shown by animal models is the use of in vitro models which primarily use monolayer cell cultures as a testing medium (Karamichos et al., Investig. Ophthalmol. Vis. Sci., 51 (2010) 1382-1388; Chipev et al., BMC Dermatol., 2, 13 (2002)). However, these models lack in their ability to replicate the precise 3D structure, ECM and cellular alignments of scar tissue. Further, they are also unable to provide the graded distribution of growth factors and their controlled release that is required for targeting the gene expression and protein expression specific to scar tissue type and stages.

To this end, a 3D bioprinted scar tissue model is provided herein, to overcome the specific limitations described in the models above. The 3D bioprinted scar tissue described herein provides the specific parallel ECM (e.g., collagen fibrillar matrix) alignment integral to scar tissue development, and replicates the in vivo gene and protein expression pattern through the unique combination of 3D bioprinting coupled with a specific bioink composition along with the biomimetic crosslinking of optimised cytokines to replicate natural scar tissue.

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Computer-aided design (CAD) refers to the use of computer systems to design, modify, optimize and analyse designs. In the present disclosure, the design refers to a model of scar tissue which may be generated by a computing device coupled to the system 100 (FIG. 1), and may be based on CT imaging, MRI imaging, and combinations thereof, including other imaging methods known to ordinary persons skilled in the art.

The bioink or bioink composition referred herein is a biomaterial-based matrix that supports the proliferation, differentiation, and adhesion of the cells which are a component of the bioink composition. In the present disclosure, the bioink comprises at least one polypeptide, at least one cytokine, and at least one cell population selected form the group consisting of epidermal cells, dermal cells, and tissue specific fibroblastic cells.

Polypeptide refers to a linear organic polymer consisting of a large number of amino-acid residues bonded together in a chain, forming part of (or the whole of) a protein molecule. For the purposes of this disclosure, the term polypeptide is to be used interchangeably with protein.

Cytokines refer to the broad category of proteins that are growth factors involved in a range of cell-signalling functions. These comprise chemokines, interferons, interleukins, lymphokines, and tumour necrosis factors, among others.

3D bioprinting refers to the direct-write-assembly of 3 dimensional structures. Specifically, it refers to fabrication methods that use a computer-controlled system, which moves a pattern-generating device, such as an ink deposition nozzle, to create materials with specific and desired architecture and composition (Lewis, J. A., Material Matters, 2008, 3.1, 4).

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products, compositions, and methods are clearly within the scope of the disclosure, as described herein.

Although the subject matter has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter. It is therefore contemplated that such modifications can be made without departing from the spirit or scope of the present subject matter as defined.

The present subject matter relates to a method of fabricating a 3D bioprinted scar tissue, the method comprising: 3D bioprinting of at least one layer of a bioink composition, using a computer-assisted design model (CAD), wherein the bioink comprises at least one polypeptide, at least one cytokine, and at least one cell population selected form the group consisting of epidermal cells, dermal cells, and/or tissue specific fibroblastic cells.

The 3D bioprinted scar tissue obtained from the method described herein, is fabricated using extrusion-based bioprinting methods, a bioink composition comprising at least one polypeptide, at least one cytokine, and at least one cell population selected form the group consisting of epidermal cells, dermal cells, and/or tissue specific fibroblastic cells.

The present subject matter includes an apparatus for bioprinting a 3D bioprinted scar tissue comprising: (a) a printing substrate, (b) a 3D bioprinter with at least one nozzle for 3D bioink printing, and (c) a bioink composition comprising at least one protein, at least one cytokine, and at least one cell population selected form the group consisting of epidermal cells, dermal cells, and/or tissue specific fibroblastic cells.

Figure 2:
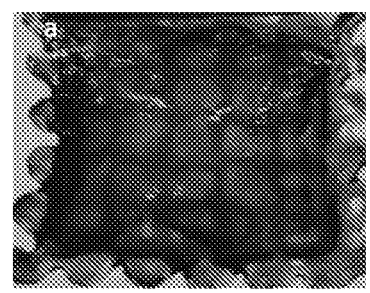
FIG. 2 shows a 3D bioprinted in vitro scar tissue, in accordance with an embodiment of the present disclosure.
Figure 5:
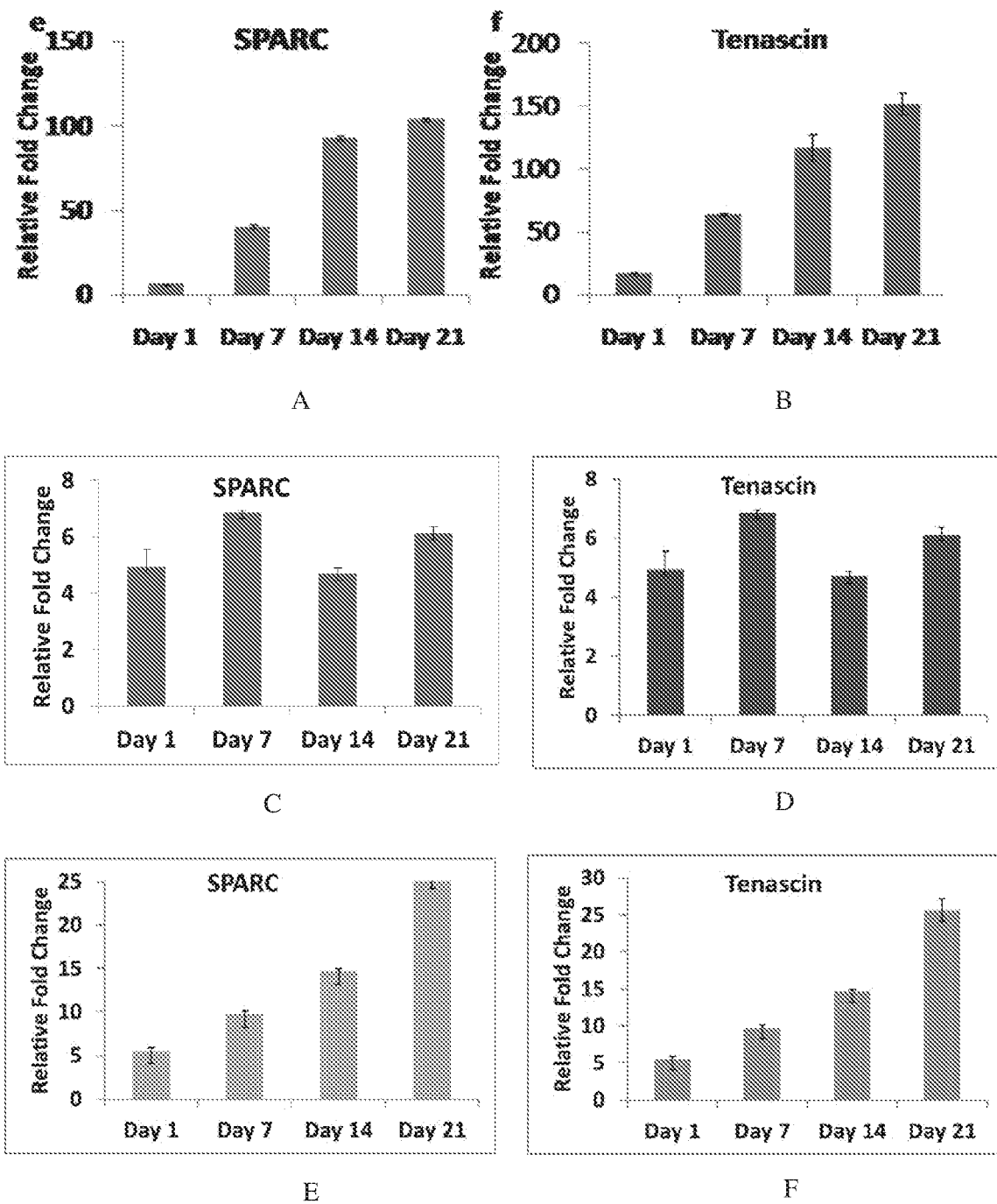
FIG. 5 shows the expression of the myofibroblast marker genes SPARC and Tenascin in 3D bioprinted scar tissue. 5(A) and (B) show the expression of the genes in 3D bioprinted skin scar tissue. 5(C) and 5(D) show the expression of the genes when cytokines are not added to the 3D bioprinted scar tissue. 5(E) and 5(F) show the expression of the genes when cytokines are exogenously added to the 3D printed scar tissue, in accordance with an embodiment of the present disclosure.

The apparatus of the present subject matter comprises a 3D bioprinter which utilizes a CAD model of said 3D bioprinted scar tissue. The manner in which the 3D bioprinted scar tissue is fabricated is illustrated in FIG. 1. Generally, 3D printing systems are referred to as additive manufacturing systems. FIG. 5 illustrates a block diagram of an additive manufacturing system 100 (referred to as the system 100) for generating one or more 3D objects, such as constructs as shown in FIG. 2. The block diagram illustrates logical blocks representing functional entities which may be present in the system 100. The block diagram does not indicate any specific arrangement of such functional elements nor does it represent the manner in which such elements may be interconnected with each other. Any arrangement of blocks may be implemented without deviating from the scope of the present subject matter. In the present example, the system 100 is maybe linked to a computer for the generation of the CAD model which is used to guide the system 100. The system 100 includes a print assembly 102 and a work area 104. The print assembly 102 in turn may include a print carriage unit 103. The print assembly 102, i.e., print carriage unit 103, operate over the work area 104 deposit build material and any other suitable agents, layer-by-layer, in order to generate a 3D object, such as the 3D bioprinted scar tissue of the present invention.

The additive manufacturing, i.e., 3D bioprinting is based on a CAD model which may be generated by a computing device coupled to the system 100 and may be based on CT imaging, MRI imaging, and combinations thereof, including other imaging methods known to ordinary persons skilled in the art.

The system 100 performs the 3D bioprinting based on a plurality of printing parameters indicative of printer settings of the 3D bioprinter. The printer parameters include a printer nozzle diameter for the 3D bioprinting and an extrusion pressure at the printer nozzle for the 3D bioprinting. The printer nozzle diameter is in the range of 40 (micrometers) μm-260 (micrometers) μm. The extrusion pressure is the pressure at the printer nozzle at which the bioink is extruded during the 3D bioprinting. The bioprinting is carried out at an extrusion pressure in the range of 1 pound per square inch (psi)-40 pounds per square inch (psi).

In a further implementation of the present disclosure, the nozzle diameter is in the range of 100 μm-200 μm, and the extrusion pressure is in the range of 10 psi-40-psi.

In another implementation of the present disclosure, the nozzle diameter is in the range of 150 μm-250 μm, and the extrusion pressure is in the range of 20 psi-40 psi.

Further, the 3D bioprinting of the apparatus of the present disclosure is carried out under sterile conditions. The 3D bioprinter prints the 3D scar construct on a substrate. The substrate may include glass slides, plastic tissue culture plates, sterile glass coverslips, and the like. The temperature for 3D bioprinting is maintained in the range of 20° C.-35° C.

Returning to the fabrication of the 3D bioprinted scar tissue of the present disclosure, the bioink of the present disclosure is deposited in a layer-by-layer manner at a temperature in the range of 20° C.-35° C., on a suitable substrate, as described herein, to form the in vitro 3D bioprinted scar tissue. The thickness of the final bioprinted scar tissue construct is preferably in the range of 10 millimetre (mm)-25 millimetre (mm), but can be varied from a few micrometres to millimetres depending upon the user's preference and end-product use. The thickness of a layer of the bioprinted scar tissue can be varied in the range of 10 μm-400 μm.

In a further implementation, the thickness of the construct is in the range of 50 μm-300 μm, or 100 μm-400 μm, or 50 μm-150 μm, or 200 μm-400 μm.

In an example implementation, the first layer is fabricated by depositing the first layer of the bioink composition. In such a manner, additional layers of the bioink are deposited each layer over the previous layer, the process being carried out within the sterile environment, at an extrusion pressure in the range of 1 psi-40 psi, at a nozzle diameter in the range of 40 μm-260 μm, within a temperature in the range of 20° C.-35° C., on a suitable substrate.

The present subject matter includes a bioink composition comprising at least one protein, at least one cytokine, and at least one cell population selected form the group consisting of epidermal cells, dermal cells, and tissue specific fibroblastic cells. The bioink composition is prepared such that there is a multimeric complex formation among the amino acid sequences on the bioink protein, cytokine receptors on cell surface and the cytokines. This higher order complex formation in the bioink triggers ligand-induced cellular signalling pathways and post-translational modifications. Further, this allows a slow release of the cytokines in the developing 3D bioprinted scar tissue. 3D bioprinting technology further helps to control and optimise the specific orientation of cells and deposition of ECM in a similar aligned manner. This allows near-perfect replication of natural scar tissue, as the 3D bioprinted in vitro scar tissue obtained exhibits excessive synthesis of ECM synthesis and deposition, matrix stiffening, and controlled level of cellular and matrix contraction which are characteristics of scar tissue. 3D bioprinting of the bioink allows close replication of the architecture and composition of natural scar tissue allowing for the use of the scar tissue as an in vitro model for further research and investigation.

In an example implementation, the protein of the bioink composition comprises at least one polypeptide selected from the group comprising of silk fibroin protein, gelatin, keratin, fibrin, laminin, lamins, extensins, actins, fibrillins, claudins, alaunins, tublins, hyaluronic acid, chondroitin sulphate, collagen, and combinations thereof.

In a further implementation, the at least one polypeptide of the bioink composition is preferably silk. More preferably, the protein is a silk protein conjugate wherein the silk protein is cross-linked with at least one conjugate.

In an example implementation, the conjugate is selected from the group consisting of gelatins, keratins, fibrin, laminin, lamins, extensins, actins, fibrillins, claudins, alaunins, tublins, hyaluronic acid, chondroitin sulphate, collagen, and combinations thereof.

In an embodiment of the present disclosure, the protein of the bioink comprises silk-gelatin, silk-keratin, and other such silk protein-based cross-linked proteins.

In a further implementation, the polypeptide of the bioink composition is mixed with nutritional culture selected from the group consisting of DMEM, RPMI, α-MEM, and combinations therefore. The protein is mixed at a concentration in the range of 5%-20% w/v with respect to the bioink.

In an example implementation, the protein concentration in the bioink is at a concentration in the range of 10%-20%, or 15%-20%, or 5%-10%, or 5%-15%.

The bioink further comprises at least one cell population selected form the group consisting of epidermal cells, dermal cells, and tissue specific fibroblastic cells, which are added to the protein and media composition. In an implementation of the present invention, the at least one cell population is selected from the group consisting of skin fibroblasts, corneal fibroblasts, renal fibroblasts, cardiac fibroblasts, bone fibroblasts, fibrocartilage, and combinations thereof. The choice of the cell suspension to be added is dependent on target organ or the location which the in vitro scar tissue development is to replicate. For example, for a corneal 3D bioprinted scar tissue model, corneal fibroblasts may be chosen; for a renal 3D bioprinted scar tissue model, cells chosen include renal fibroblasts and for a cardiac 3D bioprinted scar tissue model cells chosen include cardiac fibroblasts and for a tracheal scar model tracheal fibroblast may be chosen.

In an implementation of the present disclosure, the at least one cell population, is added to the protein and the media of the bioink at a concentration in the range of $1\times10^3$-$1\times10^7$ cells/ml.

Further, cell population can also be added at a concentration in the range of $1\times10^3$-$1\times10^4$ cells/ml, or $1\times10^3$-$1\times10^5$ cells/ml, or $1\times10^3$-$1\times10^6$ cells/ml.

Next for the preparation of the bioink composition, silk protein is conjugated in a biomimetic manner, where the cytokine is selected from the group consisting of EGF, FGF, TGF-β1, IL-1 β, TNF-α, IL-4, IL-6, IL-8, IL-10, CTGF, and combinations thereof. This is followed by the cross-linking of silk protein to at least one other protein, for instance, silk-gelatin, silk-keratin, silk-collagen and the like, is facilitated by the addition of at least one oxidase enzyme. The oxidase enzyme oxides the accessible tyrosine residues of proteins (silk-gelatin, silk-keratin and silk-collagen) into reactive o-quinone moieties without breaking the peptide bond. This induces the solution-to-hydrogel conversion of the protein, or the cross-linked protein such as silk-gelatin, silk-keratin, as disclosed in the present invention.

In an example implementation, the enzyme is selected from the group comprising of tyrosinase, peroxidase, transglutaminase, cysteine protease, polyphenol oxidase, catechol oxidase, hexose oxidase, and combinations thereof.

The composition so obtained in the previous steps, comprising the protein, at least one cell population selected form the group consisting of epidermal cells, dermal cells, and tissue specific fibroblastic cells, cytokines and the oxidase in the nutritional medium base is then mixed together to modulate secondary conformations of silk protein and other associated proteins. This promotes the hydrophobic interactions and electrostatic interactions between amino acids in neighbouring polymer chains and induce gelation. Mixing of the components of the bioink composition is carried out by methods comprising, sonication, stirring, shaking on rotor, and the like.

All the steps described above involved in the preparation of the bioink, including addition of other protein(s), nutritional media, epidermal cells, and enzymes, further mixing the components to induce gelation, are carried out in sterile conditions, preferably within a laminar flow hood. The bioink composition obtained, by the methods described above, is extruded through the 3D bioprinter as described in the present disclosure. 3D bioprinting is carried out by extrusion based bioprinter using a CAD model and a deposition syringe and robotic platform to guide the extrusion of the bioink. The bioink is extruded at an extrusion pressure in the range of 1 psi-40 psi, at a nozzle diameter in the range of 40 μm-260 μm, within a temperature in the range of 20° C.-35° C., on a suitable substrate. The thickness of the final bioprinted scar tissue construct is preferably in the range of 10 millimetre (mm)-25 millimetre (mm), but can be varied from a few micrometres to millimetres depending upon the user's preference and end-product use. The thickness of a single layer of the bioprinted scar tissue can be varied in the range of 10 μm-400 μm. The number of layers of bioink deposition can be varied upon the user's choice as defined in the CAD model. The 3D bioprinted scar tissue obtained maybe kept for a period of 1 week to 6 weeks, within a carbon dioxide ($CO_2$) incubator maintained at a temperature in the range of 37° C. (degrees Celsius). The 3D bioprinted in vitro scar tissue of the present disclosure does not require any further supplementation or addition of nutrients or biomaterial and is a self-sustaining tissue structure.

The 3D bioprinted scar tissue of the present disclosure obtained by the process as described above has features equivalent to natural scar tissue. The 3D bioprinted scar tissue can simulate the inflammatory microenvironment of the target scar tissue and can also simulate the extensive cellular contraction associated with scar tissue.

The 3D bioprinted scar tissue of the present disclosure has the precise architecture with an optimised biomimetic cytokine attachment strategy and exhibits controlled and sustained release of cytokines. This allows for the possibility for controlled differentiation of the cell population in the in vitro scar tissue. Further, the effect of optimised matrix chemistry, precise cellular orientation as well the control over mechanical forces of the cells as exerted by matrix stiffness helped to simulate the key features of the scar tissue and further modulated the scar specific gene and protein expression in the 3D bioprinted in vitro scar model. Further, the 3D bioprinted scar tissue shows immense prospects to attain control over pore geometry that helped to replicate vascular and interstitial flow mechanics.

In an example implementation, the 3D bioprinted scar tissue of the present disclosure shows the expression of specific marker genes of scar tissue. The 3D bioprinted scar tissue shows the expression of alpha-smooth muscle actin, which is a marker of myofibroblasts; it also shows fibrotic gene expression profile of the target scar tissue.

In an implementation of the present disclosure, the 3D bioprinted scar tissue is a skin scar tissue equivalent.

In an implementation of the present disclosure, the 3D bioprinted scar tissue is a renal scar tissue equivalent.

In an implementation of the present disclosure, the 3D bioprinted scar tissue is a cardiac scar tissue equivalent.

In an implementation of the present disclosure, the 3D bioprinted scar tissue is a corneal scar tissue equivalent.

In an implementation of the present disclosure, the 3D bioprinted scar tissue is a tracheal scar tissue equivalent.

Although the subject matter has been described with reference to specific embodiments, this description is not meant to be construed in a limiting sense.

Various modifications of the disclosed embodiments, as well as alternate embodiments of the subject matter, will become apparent to persons skilled in the art upon reference to the description of the subject matter. It is therefore contemplated that such modifications can be made without departing from the spirit or scope of the present subject matter as defined.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

The subsequent paragraphs depict the preparation of 3D bioprinted in vitro model of cornea and skin scar tissue. The method has been optimized with respect to: (i) cytokine attachment to the bioink, (ii) effect of matrix chemistry, (iii) cellular orientation, (iv) mechanical forces (such as matrix compliance and stiffness), and (v) pore geometry to replicate vascular and interstitial flow mechanics. It is therefore understood that a person skilled in the art will be able to prepare 3D bioprinted fibrotic tissue specific to any organ by employing the method as described herein.

Example 1

3D Bioprinted in Vitro Model of Corneal Scar

The present subject matter describes the process of fabricating a 3D bioprinted in vitro corneal scar tissue. In an example implementation, collagen type-I (A1048301, Gibco) was obtained and mixed in DMEM (CC 3004, Cellclone). The final concentration of the protein was in the range of 5% to 20% w/v in the media. Corneal fibroblast cells were added at a concentration in the range of $1\times10^3$-$1\times10^7$ cells/ml. Further, cytokines TGF-$\beta$1, IL-6, and IL-8 were added to the hydrogel at a concentration in the range of 1 ng/ml-1 µg/ml. The bioink was incubated at 37° C. to allow self-assembly and crosslinking of collagen prior to bioprinting. The bioink so obtained was extruded at an extrusion pressure in the range of 1 psi-40 psi, at a nozzle diameter in the range of 40 µm-260 µm, within a temperature in the range of 20° C.-35° C., on a suitable substrate. The thickness of the final bioprinted scar tissue construct was in the range of 10 mm-25 mm. The thickness of a single layer of the bioprinted scar tissue was varied in the range of 10 µm-400 µm.

Figure 3:
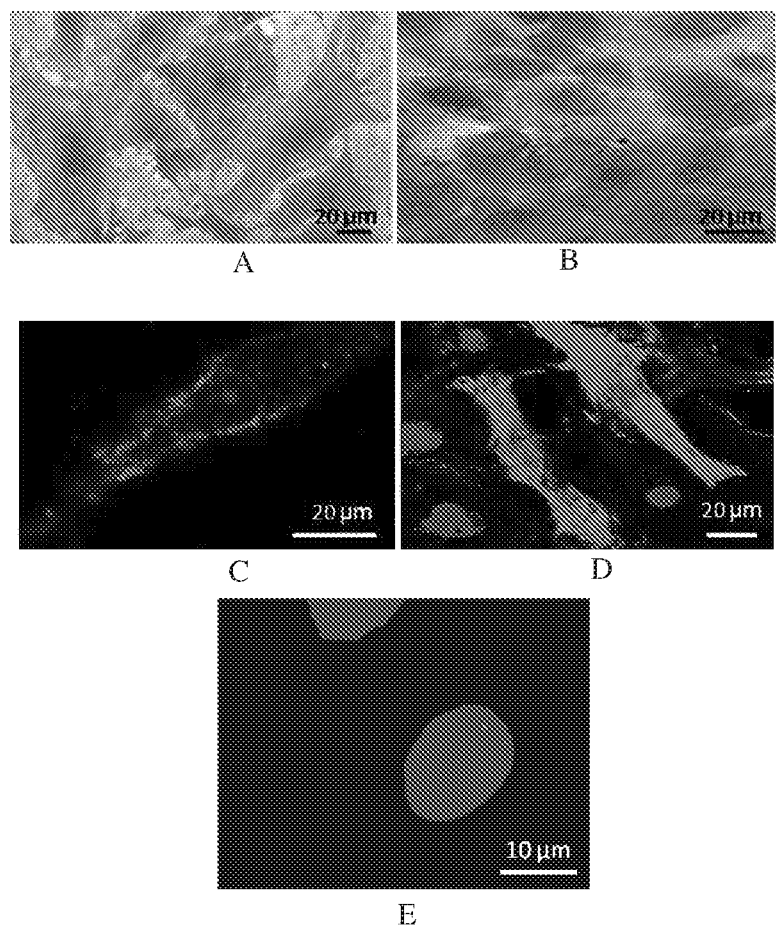
FIG. 3 illustrates the properties of 3D bioprinted corneal scar tissue. 3(A) and 3(B) show the histology of 3D bioprinted corneal scar tissue. 3(C) shows the expression of Collagen type I. 3(D) shows the arrangement of α-smooth muscle actin (SMA) fibre and the expression of α-SMA protein. 3(E) shows that the α-SMA protein does not express in the 3D bioprinted corneal scar tissue without cytokines. 3(F) and 3(G) show the expression of myofibroblast marker genes SPARC and Tenascin in the 3D bioprinted corneal scar tissue, in accordance with an embodiment of the present disclosure.
Figure 3:
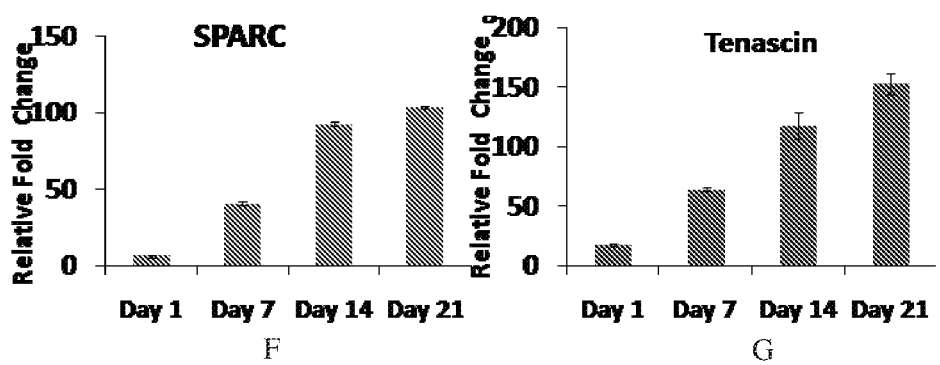

A number of in vitro characterization techniques were performed including the quantitative real time-reverse transcriptase PCR (qRT-PCR) and immunofluorescence analysis (IFC) to determine the extent of fibroblast to myofibroblast differentiation and subsequent formation of the respective scar tissue. Histological analysis revealed the presence of cells with spread morphology (FIG. 3A) and the presence of glycosaminoglycans (FIG. 3B) Immunofluorescence based protein expression analysis visualised using high end fluorescence microscopy revealed the synthesis of collagen I and $\alpha$-SMA (marker of myofibroblasts differentiation) (FIGS. 3C and 3D). However, without the presence of cytokines, expression of $\alpha$-SMA is not observed (FIG. 3E), thereby enunciating the requirement for the cytokines.

qRT-PCR based gene expression analysis revealed the expression of fibrotic markers like SPARC and Tenascin (FIGS. 3G and 3H) in the developed 3D bioprinted scar model demonstrating that the in vitro scar tissue shows features characteristic of natural scar tissue and can be used as an in vitro model for further research and analysis.

Example 2

3D Bioprinted in Vitro Model of Skin Scar

The present subject matter describes the process of fabricating a 3D bioprinted in vitro skin scar tissue. In an example implementation, using silk-collagen type I. The procedure for preparation of the silk-protein conjugate can be carried out by a person skilled in the art (Chawla et al., Bioprinting, 7, 2017, 1-13). Briefly, was prepared by mixing 5% w/v of autoclaved silk fibroin solution and 5 wt % of collagen powder sterilized using ethanol and the 5× silk-collagen protein (Gibco) was added in 10× media (Sigma) and 10% fetal bovine serum (FBS) (Himedia).

This was then mixed, preferably by sonication, and incubated at 37° C. for 15 min for uniform dissolution. 10 U to 1000 U, preferably 800 U of mushroom tyrosinase (Sigma) were added to a 600 µl suspension of the silk-collagen type-I protein for enzymatic cross-linking earlier to cell encapsulation. Skin fibroblasts were added at a concentration in the range of 1×10³-1×10⁷ cells/ml. Further, cytokines TGF-β1 (GF111, Millipore), IL-6 (IL006, Millipore), IL-8 (IL010, R&D systems) were added to the hydrogel at a concentration in the range of 1 ng/ml-1 µg/ml. The bioink so obtained was extruded at an extrusion pressure in the range of 1 psi-40 psi, at a nozzle diameter in the range of 40 µm-260 µm, within a temperature in the range of 20° C.-35° C., on a suitable substrate. The thickness of the final bioprinted scar tissue construct was in the range of 10 mm-25 mm. The thickness of a single layer of the bioprinted scar tissue was varied in the range of 10 µm-400 µm.

Figure 4:
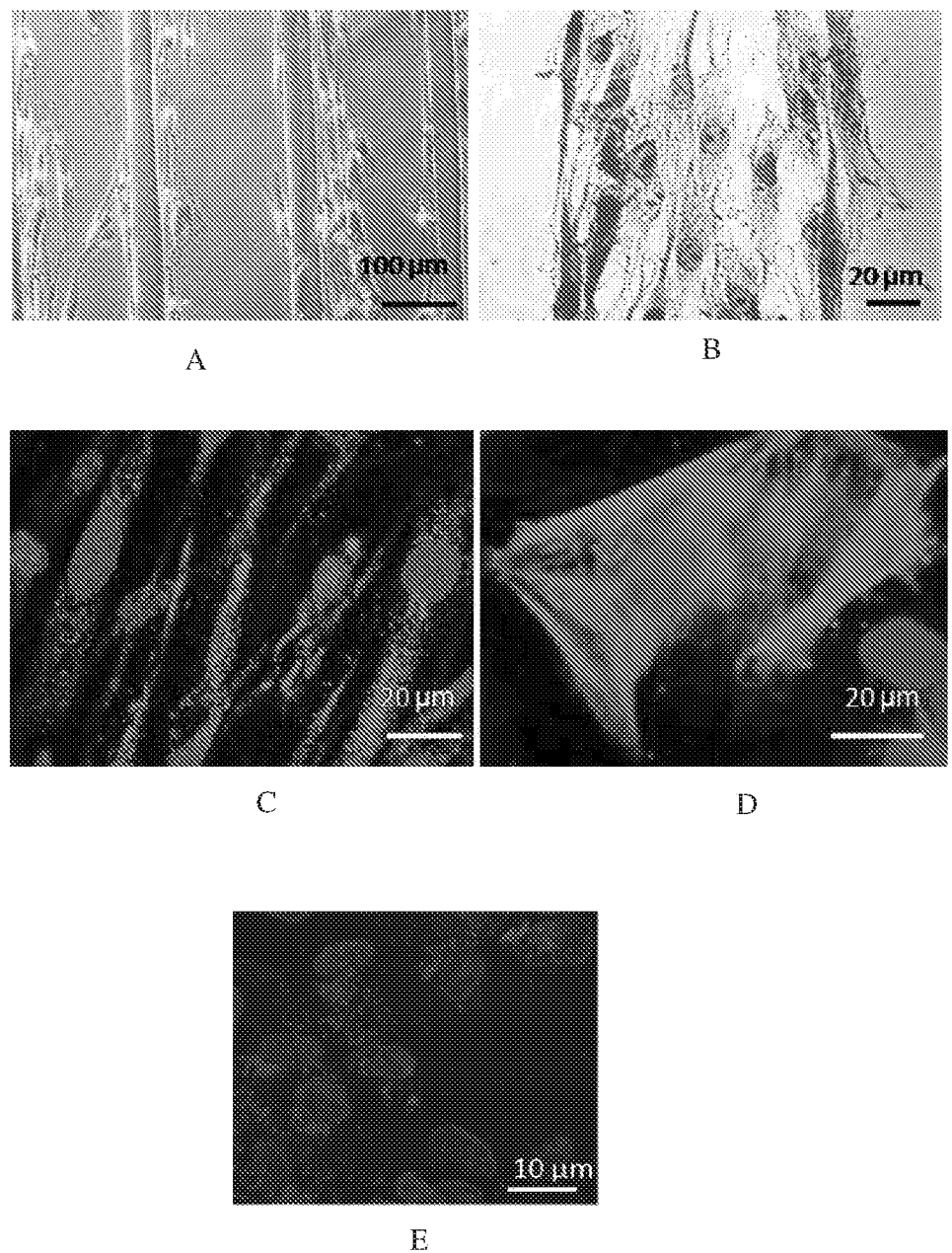
FIG. 4 shows a 3D bioprinted skin scar tissue. 4(A) and (B) show the histology and parallel arrangement of the cells in a 3D bioprinted skin scar tissue. 4(C) shows the expression of collagen type I in a parallel aligned manner. 4(D) show the arrangement of α-SMA fibres and the expression of α-SMA protein. 4(E) shows the random arrangement of cells and corresponding expression of Collagen type I without 3D bioprinting, in accordance with an embodiment of the present disclosure.

In vitro characterization techniques were performed including the quantitative real time-reverse transcriptase PCR (qRT-PCR) and immunofluorescence analysis (IFC) to determine the extent of fibroblast to myofibroblast differentiation and subsequent formation of the respective scar tissue. Histological analysis revealed the precise alignment of the cells in the developed 3D bioprinted scar model (FIGS. 4A and 4B) which is very similar to naturally occurring scar tissue. IFC based protein expression analysis visualised using high end fluorescence microscopy revealed the synthesis of collagen I and α-SMA (marker of myofibroblasts differentiation) (FIGS. 4C and 4D) demonstrating that the 3D bioprinted in vitro scar tissue model closely replicates the features of naturally occurring scar tissue. Further, without 3D bioprinting, the precise architecture of scar tissue was not replicated as is seen in FIG. 4(E), where the cells are not aligned and there is a random arrangement of cells and thus randomly oriented collagen type I production.

qRT-PCR based gene expression analysis revealed the expression of fibrotic markers like SPARC and Tenascin in the developed 3D bioprinted scar model (FIGS. 5A and 5B). Further, without the addition of cytokines, there was nominal expression of both fibrotic markers (FIGS. 5C and 5D). To illustrate, in the presence of cytokines, SPARC and Tenascin show an approximately 100 and 150 fold increase by day 21, while in the case where no cytokines were added, the SPARC and Tenascin show only approximately 8 fold increase in gene expression by day 21. Therefore, the data clearly demonstrate that the specific bioink composition disclosed in the present invention allows for very close replication of the natural physiological and architectural characteristics of scar tissue.

Further, the specific composition of bioink is such that the there is a complex formation between the protein and the cytokine components of the bioink. This helps to mimic the in vivo anchoring of the cytokines to the ECM so as form the multimeric complex with focal adhesion points at the cell-matric interface. This enables the slow and controlled release of cytokines into the cell media and triggers the cell signalling pathways which are temporal in nature. This property is demonstrated in FIGS. 5E and 5F, where the cytokines are exogenously added to the media, rather the bioink matrix itself to allow for conjugation. As seen in FIGS. 5E and 5F, the expression of the scar tissue markers SPARC and Tenascin, is higher than when cytokines are not added (FIGS. 5C and 5D), however, the expression of the markers is much lower than when the cytokines are added in the bioink, showing almost an 8 fold difference in gene expression on day 21 (FIGS. 5E and 5F).

Advantages of the Present Invention

The present invention provides a 3D bioprinted in vitro scar tissue which demonstrates precise simulation of the complex 3D architecture, number of layers and cells corresponding to the tissue of interest that showed similarity with the in vivo like gene and protein expression. This is made possible by the unique combination of a specialized bioink composition comprising a polypeptide-cytokine conjugate and epidermal and dermal cells or tissue specific fibroblasts, together with specific 3D bioprinting parameters which allow for the development of the presently disclosed scar tissue which demonstrated in vivo scar tissue-like properties. Further, the presently disclosed 3D bioprinted scar tissue can be customized for a specific target site by using the desired cell-type. The present invention is successful in replicating the following important characteristics similar to in vivo characteristics: (a) cellular alignment and precise control over orientation of newly synthesized ECM fibrous proteins, (b) presentation of specific biochemical signals, their sustained and controlled release and (c) controlled contractility of cells will lead to development of precise spatiotemporally controlled morphogen gradient, in order to replicate specific stages of scar in the context of specific tissue type.

What is claimed is:

1. A method of fabricating a 3D-bioprinted in-vitro model of scar, the method comprising:
    3D bioprinting layer-by-layer of a bioink composition using a computer-assisted design model,
        wherein the bioink composition comprises at least one polypeptide selected from the group consisting of silk protein conjugate, collagens, gelatins, and combinations thereof, at least one cytokine selected from the group consisting of IL-6, IL-8, IL-10, TGF-β1, and combinations thereof, and at least one cell population that is a tissue specific fibroblast cells of the tissue selected from the group consisting of skin and corneal,
        wherein the at least one polypeptide is at a concentration in the range of 5%-20% w/v, with respect to the bioink composition, and the at least one cell population is at the concentration in the range of 1×10³-1×10⁷ cells/ml, and
        wherein the 3D bioprinting is carried out at an extrusion pressure in the range of 1 PSI-40 PSI, at a temperature in the range of 20° C.-35° C., with a printer nozzle having a diameter in the range of 40 µm-260 µm.

2. A method of fabricating a 3D-bioprinted in-vitro model of scar of claim 1, wherein the layer has a thickness in the range of 10 µm-400 µm.

3. The method of fabricating a 3D-bioprinted in vitro model of scar of claim 1, wherein the at least one cytokine is at a concentration in the range of 1 ng/ml-1 µg/ml, with respect to the composition.

4. The method of fabricating a 3D-bioprinted in vitro model of scar of claim 1, wherein the bioink composition further comprises at least one nutritional medium selected from the group consisting of DMEM, RPMI, α-MEM, and combinations thereof.

5. The method of fabricating a 3D-bioprinted in vitro model of scar of claim 1, wherein the bioink composition further comprises at least one enzyme selected from the group comprising tyrosinase, peroxidase, transglutaminase, cysteine protease, polyphenol oxidase, catechol oxidase, hexose oxidase, and combinations thereof.

* * * * *